US008377061B1

(12) United States Patent
Hajianpour

(10) Patent No.: US 8,377,061 B1
(45) Date of Patent: *Feb. 19, 2013

(54) EXTERNAL FIXATION APPARATUS WITH ADJUSTABLE PIN CLAMPING MEANS

(75) Inventor: Mohammed A. Hajianpour, Fort Lauderdale, FL (US)

(73) Assignee: Nutek Orthopaedics, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/661,563

(22) Filed: Mar. 19, 2010

Related U.S. Application Data

(63) Continuation of application No. 11/893,582, filed on Aug. 16, 2007, now Pat. No. 7,717,916.

(51) Int. Cl.
*A61F 4/00* (2006.01)
(52) U.S. Cl. .......................... 606/59; 606/54
(58) Field of Classification Search .......... 606/53–59, 606/70–71, 99, 268, 280–297
See application file for complete search history.

(56) References Cited

U.S. PATENT DOCUMENTS

| 4,127,119 | A | * | 11/1978 | Kronner | 606/56 |
|---|---|---|---|---|---|
| 4,554,915 | A | | 11/1985 | Brumfield | |
| 4,895,141 | A | * | 1/1990 | Koeneman et al. | 606/54 |
| 5,127,914 | A | * | 7/1992 | Calderale et al. | 606/65 |
| RE34,985 | E | | 6/1995 | Pennig | |
| 5,443,464 | A | * | 8/1995 | Russell et al. | 606/54 |
| 5,501,684 | A | * | 3/1996 | Schlapfer et al. | 606/301 |
| 5,779,703 | A | | 7/1998 | Benoist | |
| 6,283,969 | B1 | * | 9/2001 | Grusin et al. | 606/280 |
| 7,147,639 | B2 | | 12/2006 | Berki et al. | |
| 7,153,302 | B1 | | 12/2006 | Hajianpour | |
| 2003/0225407 | A1 | * | 12/2003 | Estrada, Jr. | 606/54 |
| 2005/0043730 | A1 | * | 2/2005 | Janowski et al. | 606/56 |

FOREIGN PATENT DOCUMENTS

WO  WO 91/00111  8/1991

* cited by examiner

*Primary Examiner* — Eduardo C Robert
*Assistant Examiner* — Lynnsy Schneider
(74) *Attorney, Agent, or Firm* — Ronald V. Davidge

(57) ABSTRACT

An external fixation device for holding bone fragments in place includes a housing having a number of rotationally adjustable pin holders, each of which is held by a clamping member that simultaneously clamps the pin holder within an internal mounting surface of the housing and a bone pin within the pin holder. A first embodiment includes a number of internal mounting surfaces, each of which can include a single pin holder. A second embodiment includes one or two internal mounting surfaces, each of which holds a row of pin holders that is clamped in place by a single clamping member.

10 Claims, 4 Drawing Sheets

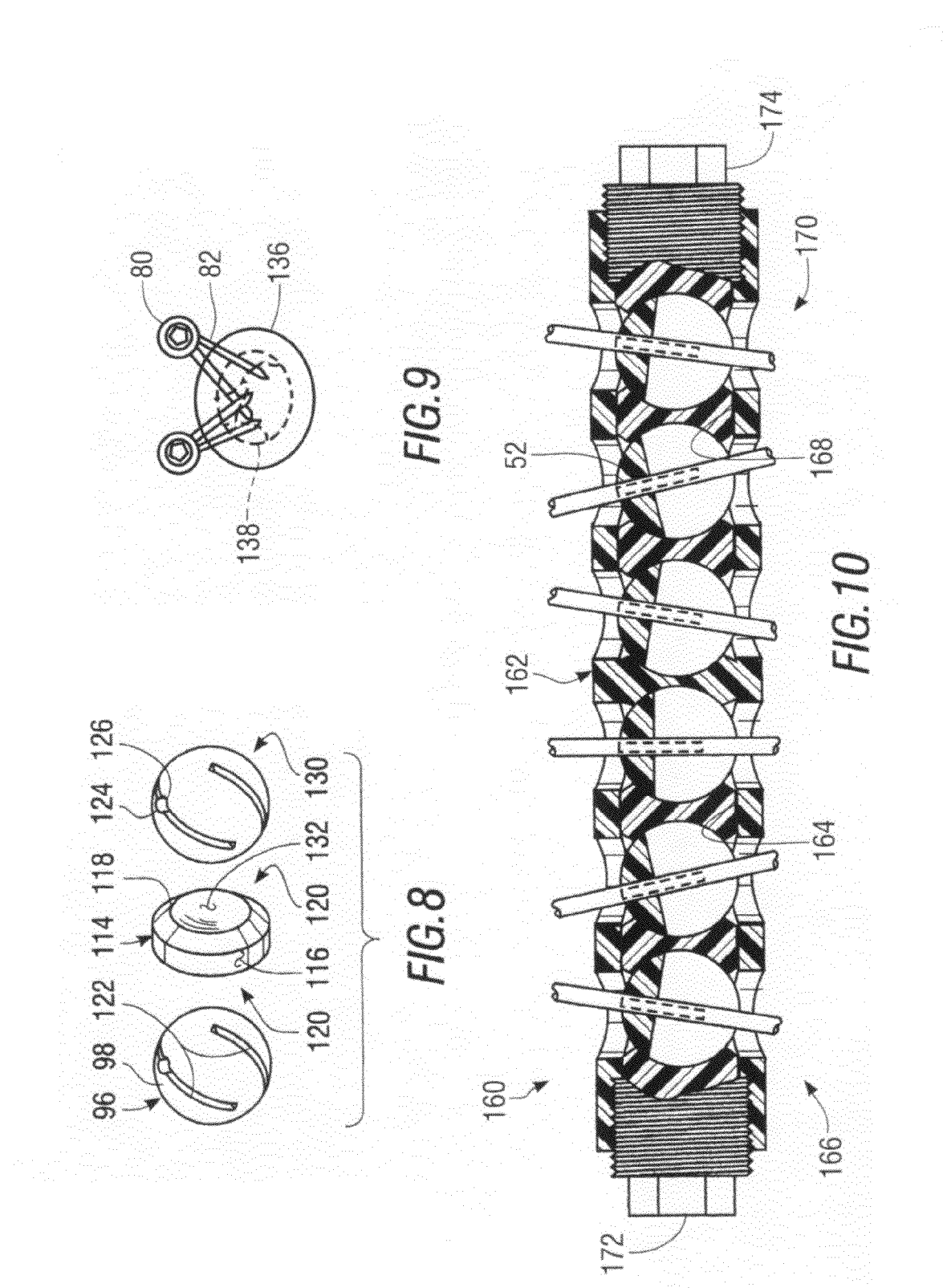

EXTERNAL FIXATION APPARATUS WITH ADJUSTABLE PIN CLAMPING MEANS

CROSS-REFERENCE TO A RELATED APPLICATION

This is a continuation of a U.S. patent application Ser. No. 11/893,582, filed Aug. 16, 2007, now issued as U.S. Pat. No. 7,717,916 B2

BACKGROUND OF THE INVENTION

1. Field of the Invention

This invention relates to apparatus for the external fixation of fractured bones, and, more particularly, to such apparatus having means for adjustably mounting and clamping a number of bone pins to a housing.

2. Summary of the Background Art

External fixation often provides the best method for holding bone fragments in place during the healing of a severe bone fracture, in which multiple bone fragments are formed. In the external fixation process, bone pins or wires ate surgically attached to the individual bone fragments and to intact sections of bone, so that a desired alignment of multiple fragments can be maintained during the healing process. The individual bone pins or wires are also attached to a frame that is external to the body to be held in a fixed configuration. Then, after the bone fragments have joined to one another in a satisfactory manner, the bone pins or wires are removed from the bones and from the body in another surgical procedure. With external fixation, an ability to hold individual bone fragments in place often makes it possible to achieve results that cannot be achieved using other conventional techniques, such as casting.

Since serious bone fractures can occur in many different ways in various parts of the body, forming various configuration of bone fragments, it is highly desirable that a device for external fixation should be configured in a variety of different ways, reducing the number of different types of fixation devices that need to be held in inventory to meet expected demands. To this end, the patent literature includes a number of descriptions of fixation devices that can be assembled from multiple elements in various ways or that can be adjusted to provide various configurational features.

One method to obtain this kind of flexibility has been to provide a plate having a number of holes defining locations in which bone pins or wires may be clamped, with only a variable subset of the holes being used in the treatment of a typical fracture. For example, U.S. Pat. No. 7,153,303 describes a fixture including several holes for clamping members to hold bone pins disposed within an elongated portion and a number of holes in a rectangular pattern, which can accommodate a variety of pin configurations. Such an arrangement is used, for example, to fasten the elongated portion of the fixture to the shaft of the radius bone within the arm and to attach vatious fragments within a broken wrist to a pattern of pins clamped within the rectangular array. A configuration for applying external fixation to a fractured tibia is also described as including a frame an elongated lower section for fastening the frame to the shaft of the tibia using bone pins extending along a straight line and an arcuate section extending from each side of the upper end of the elongated lower section for clamping bone pins extending into bone fragments within the upper portion of the tibia. U.S. Pat. No. 5,779,703 describes a bone organizer having a number of holes through which wires are attached to bone fragments.

Another method for obtaining flexibility within an external fixation device is to provide a number of clamping elements holding one or more bone pins, with the clamping elements being attached to one another by devices providing for pivotal adjustment. For example, U.S. Pat. No. 5,624,440 describes a fixture including a number of clamping elements, each of which clamps a pair of bone pins extending parallel to one another and a rod to which the clamping elements are attached by means of a pair of pivoting clamps providing for rotational adjustment and clamping about two axes perpendicular to one another. U.S. Pat. No. RE34,985 describes a fixation device having a pair of elongated carriers, each of which supports a pair of bone screws that are movable along the carrier by rotating a spindle. The carriers are joined to one another by a connector including a rigid rod and a ball at each end. The balls are received by partly spherical sockets that can be fixed relative to the balls through screws. U.S. Pat. No. 4,554,915 describes an external fixation frame including a fixation block from which one or more arms extend, with a ball and socket joint connecting each arm to the block for universal movement thereabout. Setscrews are provided for tightening the ball and socket joints. International Pat. Appl. Pub. No. WO 91/111 describes a fixation device having a pair of clamping members, each of which includes a row of holes into which bone pins may be inserted and clamped, with the clamping members being connected by a tube, into which a rod extends from one of the clamping members, while a ball from the other connecting member extends into a partially spherical hole within the tube. Setscrews are provided for clamping the rod and ball in place within the tube.

What is needed is a bone fixation device having the flexibility of adjusting the angle at which individual bone pins extend from a housing or frame, preferably with such an adjustment being provided through a clamping device that simultaneously clamps both the linear extension of the bone pin, along its length, and its angle relative to the housing or frame.

SUMMARY OF THE INVENTION

In accordance with a first aspect of the invention, apparatus is provided for external fixation of bone fragments, with the apparatus including a housing, a plurality of pin holders, a plurality of bone pins, and a clamping mechanism. The housing includes at least one internal mounting surface and a plurality of apertures. The pin holders are held within the housing. Each of the pin holders includes a pin mounting hole, a spherically rounded surface engaging at least one of the at least one internal mounting surface within the housing and at least one deformable portion. The bone pins are each held within the pin mounting hole in a pin holder within the plurality of pin holders to extend through an aperture in the plurality of apertures. The clamping mechanism holds each pin holder in the plurality of pin holders in place within the housing and deflects the deformable portion of each pin holder to hold the pin in place within the pin holder. The clamping mechanism includes at least one clamping member engaging at least one of the pin holders in the plurality of pin holders to hold the pin holder in place within the housing and simultaneously deflecting the deformable portion of the pin holder to hold the bone pin in place within the pin holder.

When the clamping member holding a pin holder in place is loosened, the pin holder can be rotated, with the spherically rounded surface of the pin holder being moved within the internal mounting surface to change the angle at which the bone pin extends outward from the housing, and the bone pin within the pin holder can be moved along a pin mounting hole within the pin holder. When the clamping member holding the pin holder in place is tightened, the pin holder is clamped within the internal mounting surface of the housing, and the pin is clamped within the pin holder.

The clamping mechanism includes a plurality of clamping members, each clamping a pin holder in the plurality of pin holders in place within the housing and deflecting the deformable portion of the pin holder to hold the pin in place within the pin holder. The housing includes a plurality of internal mounting surfaces. Each clamping member in the plurality of clamping members includes a threaded surface and an annular surface engaging the deformable portion of a pin holder in the plurality of pin holders. The housing includes a plurality of threaded surfaces, each disposed adjacent an aperture in the plurality of apertures. The threaded surface of each of the clamping members engages one of the threaded surfaces of the housing. The housing includes a vertically elongated central portion and a lateral portion extending outward and rearward from each side of an upper end of vertically elongated central portion: The vertically elongated central portion includes a first plurality of the internal mounting surfaces, while each lateral portion includes at least one of the internal mounting surfaces. As each of the clamping members is rotated in a first direction, an engagement force between the spherically rounded surface of the pin holder clamped in place within the housing by the clamping member and the internal mounting surface within the housing is increased to hold the pin holder in place within the housing, and deflection of the deformable portion of the pin holder is increased to hold the bone pin in place within the pin holder. As each of the clamping members is rotated opposite the first direction, the engagement force between the spherically rounded surface of the pin holder and the internal mounting surface within the housing is decreased to allow rotation of the spherically rounded surface of the pin holder within the internal mounting surface of the housing and to allow movement of the bone pin within the pin mounting hole of the pin holder.

BRIEF DESCRIPTION OF THE FIGURES

FIG. 8 is an exploded perspective views of adjacent pin holders and a spacer disposed therebetween within the device of FIG. 5

FIG. 9 is a partly sectional end view of a finger having two of the devices of FIG. 5 attached to bone fragments; and FIG. 10 is a cross-sectional side view of a device built in accordance with a second version of the second embodiment of the invention.

DETAILED DESCRIPTION OF THE INVENTION

Figure 1:
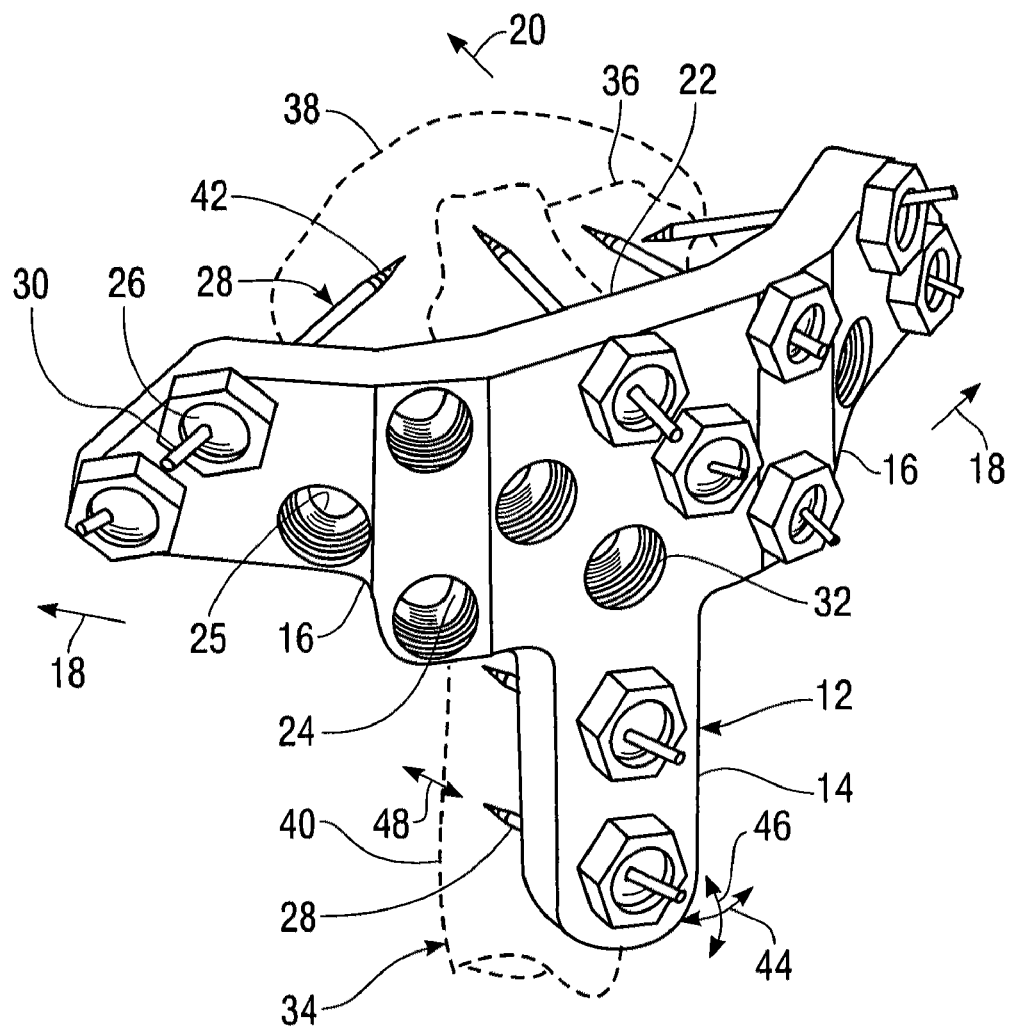
FIG. 1 is a perspective view of a device for external fixation of bone fragments, built in accordance with a first embodiment of the invention.

FIG. 1 is a perspective view of a device 10 for the external fixation of bone fragments, built in accordance with a first embodiment of the invention. The device 10 includes a housing 12 having a vertically elongated central portion 14 and a lateral portion 16 extending outward, in the directions of arrows 18, and rearward, in the direction of arrow 20, from each side of an upper end 22 of vertically elongated central portion 14: The vertically elongated central portion 14 includes a first plurality of the internal mounting surfaces 24; each of which extends outwardly from an aperture 25 within the housing 12, while each lateral portion 16 includes at least one of the internal mounting surfaces 24 extending from an aperture 25. Some of the internal mounting surfaces 24 mount pin holders 26 holding bone pins 28, with the pin holders 26 being held in place by clamping members 30 engaging threaded surfaces 32 of the housing 12. This arrangement provides for the placement of bone pins 28 at various levels extending downward from the upper end 22 of the vertically elongated central portion 14, with the lateral portions 16 being inclined relative to one another so that bone pins 28 can extend inward around a fracture area from these portions 16.

In the example of FIG. 1, the device 10 is shown with various bone pins 28 attached to a fractured humerus bone 34, holding a number of fragments 36 in place at an upper end 38 of the humerus bone 34, with bone pins 28 held within the vertically elongated central portion 14 of the housing 12 attached to the shaft portion 40 of the humerus bone 34. Each of the bone pins 28 includes a threaded end 42 that is driven into engagement with a portion of the bone 34 by a driving tool (not shown) rotating a non-circular surface (not shown) at an end of the bone pin 28 opposite the threaded end 42. After the bone pin 28 is fastened into place, the bone pin 28 is preferably cut off outwardly adjacent the pin holder 26 in which it is held to limit the distance through which the bone pin 28 extends outwardly from the device 10. The configuration of the device 10 is adjustable in several ways, with pin holders 26 being placed in a subset of the internal mounting surfaces 24, so that bone pins 28 are placed at locations appropriate for the external fixation of a particular fractured bone. In addition, the individual pin holders 26 are angularly adjustable so that each bone pin 28 can be adjusted and clamped in place through a vertical angle of adjustment 44 and through a horizontal angle of adjustment 46, with the bone pin 28 additionally being adjustable along its axis in the directions of arrows 48.

Figure 2:
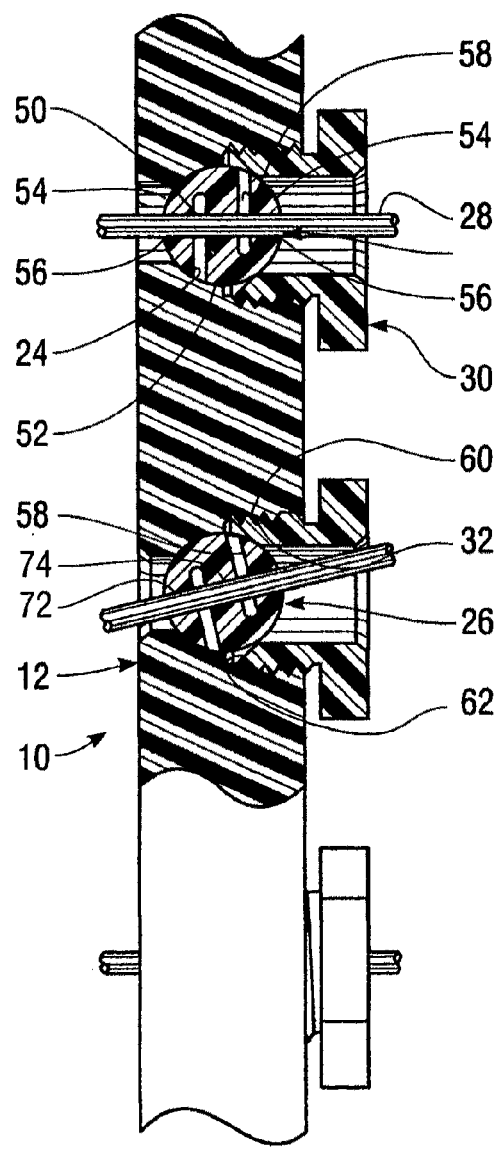
FIG. 2 is a fragmentary and partly cross-sectional lateral elevation of the device of FIG. 1.

FIG. 2 is a fragmentary and partly cross-sectional lateral elevation of the device 10, particularly showing features of the internal mounting surfaces 24 within the housing 12, of the pin holders 26, and of the clamping members 30. Each of the pin holders 26 includes a pin mounting hole 50, a spherically rounded surface 52 engaging an internal mounting surface 24 within the housing, and deformable portions 54 at each end 56 of the pin mounting hole 50. Each of the deformable portions 54 is formed by a slot 58 extending inward in a direction perpendicular to the pin mounting hole 50, extending across the pin mounting hole 50 and part of the way across the pin holder 26. Each of the of clamping members 30 clamps a pin holder 26 in place within the housing 12 and deflects the deformable portions 54 of the pin holder 26 to hold the pin 28 in place within the pin holder 26. Each clamping member 30 includes a threaded surface 60 and an annular surface 62 engaging a deformable portion 54 of a pin holder 26. The threaded surface 60 of each of the clamping members 30 engages one of the threaded surfaces 32 of the housing 12.

Thus, each of the bone pins 28 extends through an aperture 25 within the housing 12 at angles, in horizontal and vertical planes relative to the housing 12, that can be varied by rotation of the spherically rounded surface 52 of the pin holder 26 through which the bone pin 28 extends within the internal mounting surface 24. A bone pin may extend in a direction perpendicular to the aperture 25 or at an angle of inclination relative to such a direction of, for example, up to thirty degrees.

Figure 3:
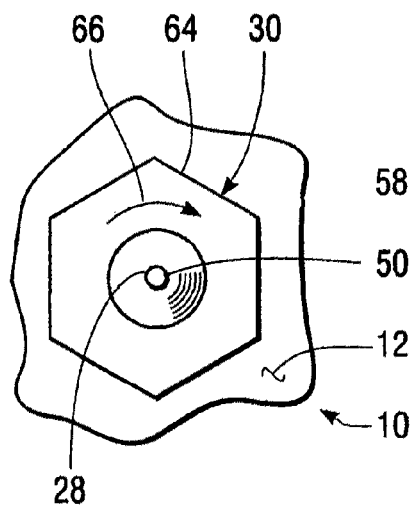
FIG. 3 is a fragmentary front elevation of the device of FIG. 1.

FIG. 3 is a fragmentary front elevation of the device 10, showing one of the clamping members 30, which is provided with a noncircular surface 64 to facilitate rotation of the clamping member 30. As the clamping member 30 is tightened by rotation in a first direction, indicated by arrow 66, an engagement force between the spherically rounded surface 52 of the pin holder 26 clamped in place within the housing 12 by the clamping member 30 and the internal mounting surface 24 within the housing 12 is increased to hold the pin holder 26 in place within the housing 12 and deflection of the deformable portions 54 of the pin holder is increased to hold the bone pin 28 in place within the pin holder 26. As each of the clamping members 30 is rotated opposite the first direction of arrow 66, the engagement force between the spherically rounded surface 52 of the pin holder 26 and the internal mounting surface 24 within the housing 12 is decreased to allow rotation of the spherically rounded surface 52 of the pin holder 26 within the internal mounting surface 24 of the housing 12 and to allow movement of the bone pin 28 within the pin mounting hole 50 of the pin holder 26. For example, the device 10 may be provided with a box wrench (not shown) for loosening and tightening the clamping members 30.

Figure 4:
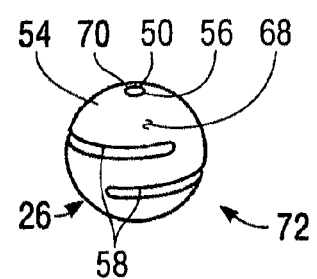
FIG. 4 is a perspective view of a pin holder within the device of FIG. 1.

FIG. 4 is a perspective view of one of one of the pin holders 26, which has a spherical external surface 68. The clamping member 30 includes a pair of slots 58 extending perpendicular to the pin mounting hole 50, inward across the pin mounting hole 50 and partly across the pin holder 26, so that a deformable portion 54 is formed between each end 56 of the pin mounting hole 50 and the slot 58 that is nearer to the end 56.

As shown in FIG. 3, the pin mounting hole 50 extends through a center of the spherical external surface 68, being divided by the slots 58 into a deflectable part 72 within each of the deformable portions 54 and a central part 74 extending between the slots 58. When the clamping member 30 is tightened by rotation in the direction of arrow 66 to increase an engagement force holding the pin holder 26 in place, the deformable portions 54 are deflected inward, bring the deflectable parts 72 of the pin mounting hole 50 out of alignment with the central part 74 thereof, so that the bone pin 28 is clamped in place within the pin mounting hole. Then, when the clamping member is loosened by rotation opposite the opposite the direction of arrow 66 to decrease the engagement force holding the pin holder 20 in place, the deformable portions 54 return outward, so that the deflectable parts 72 of the pin mounting hole 50 return into alignment with the central part 74 thereof, allowing movement of the bone pin 28 within the pin mounting hole 50. For example, the bone pin 28 may be rotated as much as thirty degrees from a central position in which the bone pin 28 extends perpendicularly from the housing 12.

Figure 5:
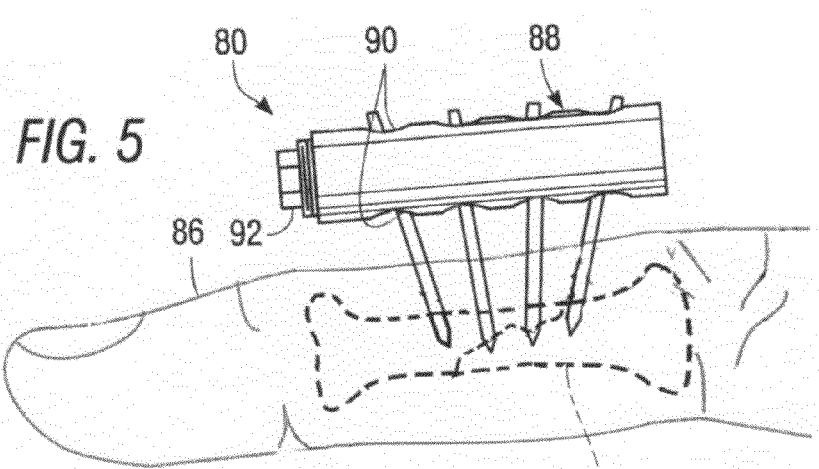
FIG. 5 is a side elevation of a device built in accordance with a first version of a second embodiment of the invention and shown attached to bone fragments within a finger.

FIG. 5 is a side elevation of a device 80 for external fixation of bone fragments, built in accordance with a second embodiment of the invention and shown with pins 82 attached to several fragments of bones 84 within a finger 86. The device 80 includes a housing 88, having a plurality of apertures 90 through which the pins 82 extend, and a first clamping member 92, which is turned to clamp the pins 82 in place within the housing 88.

Figure 6:
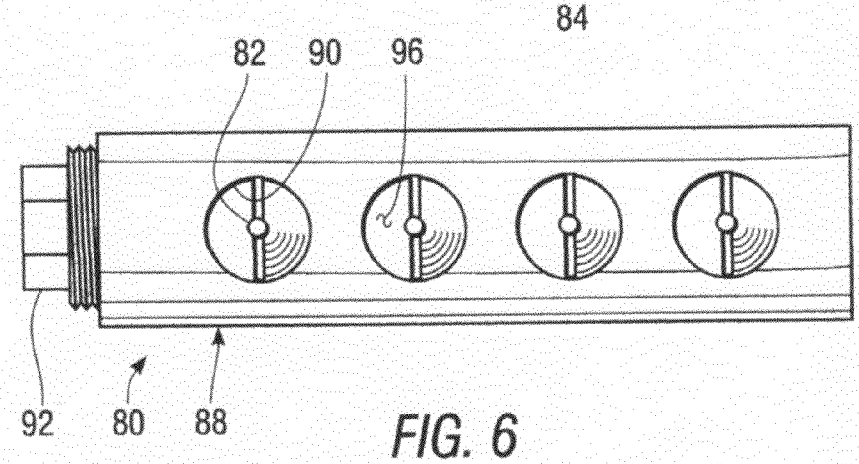
FIG. 6 is a plan view of the device of FIG. 5.
Figure 7:
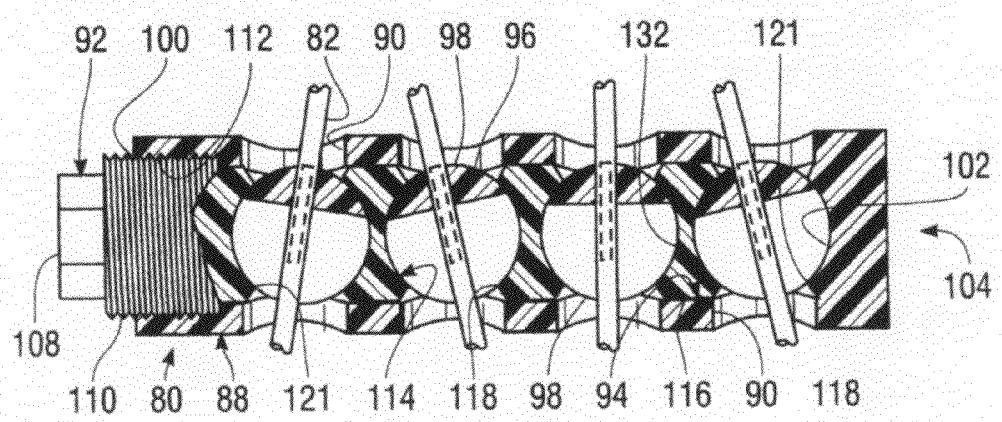
FIG. 7 is a cross-sectional side view of the device of FIG. 5.

Features of the device 80 will now be discussed with reference being made to FIGS. 6 and 7. FIG. 6 is a plan view of the device 80, while FIG. 7 is a cross-sectional side elevation thereof. The housing 88 includes a single internal mounting surface 94, with the single clamping member 92, clamping each of a plurality of pin holders 96 in place within the first internal mounting surface 94 and deflecting a deformable portion 98 of each of the pin holders 96 to hold the bone pin 82 therein in place. For example, the first internal mounting surface 94 is formed as an elongated cylinder having an open end 100 and a closed end 102, with the plurality of pin holders 96 disposed in a first row 104 within the first internal mounting surface 94. The first clamping member 92 is movable within the open end 100 of the elongated cylinder to provide a clamping force acting against the pin holder adjacent the open end 100 of the internal mounting surface 94. For example, the first clamping member is moved in the direction of arrow 106 by turning a non-circular portion 108 of the clamping member with a threaded portion 110 thereof in engagement with a threaded portion 112 of the housing 88. A clamping force, arising from the engagement between the clamping member 92 and the pin holder 96 adjacent the open end 100, is transmitted between the pin holders 96 adjacent one another within the first row 104. For example, the device 80 may be provided with a socket head wrench for loosening and tightening the clamping member 92.

FIG. 8 is an exploded perspective view of two pin holders 96 and a spacer 114 disposed between the pin holders 96. Preferably, the device 80 additionally includes a spacer 114 between each pair of pin holders 96 adjacent one another in the first row 104, with the clamping force being transmitted between the pin holders 96 adjacent one another through the spacer 114. The spacer 114 includes a peripheral surface 116 engaging the first internal mounting surface 94 of the housing 88 between adjacent apertures 90 within the housing 88 and a circular edge 118 engaging the adjacent pin holder 96 at each side 120 of the spacer 114 to hold the pin holder 96 in place within the housing 88. Without the spacers 114, the pin holders 96 would be allowed to move into the adjacent apertures 90, so that the pin holders 96 would not be rigidly mounted within the first mounting surface 94. Preferably, as shown in FIG. 7, the first clamping member 92 and the closed end 102 of the first internal mounting surface 94 additionally also include a circular edge 121 engaging the adjacent pin holder 96 to hold the pin holder 96 in place within the housing 88.

Each of the pin holders 96 additionally includes a slot 122 extending inward from each end 124 of a pin mounting hole 126 to form a part of the deformable portion 98 of the pin holder 96 at each end 124 of the pin mounting hole 128. The slots 122 at each end 124 of the pin mounting hole 128 extend along the pin mounting hole 126, being disposed perpendicular to one another. Preferably, the slots 122 are formed to extend inward, across one another in a central portion 130 of the pin holder 96, so that the central portion 130 can be deflected by contact with a concave surface 132 of the spacer 114, even if one of the slots 122 is positioned to extend between the concave surfaces 132 of spacers 114 at either side of the pin holder 96.

Thus, each of the bone pins 82 extends through an aperture 90 within the housing 88 at angles, in directions perpendicular to one another, that can be varied by rotation of the spherically rounded pin holder 96 through which the bone pin 28 extends within the internal mounting surface 94. A bone pin may extend in a direction perpendicular to the aperture 90 or at an angle of inclination relative to such a direction of, for example, up to thirty degrees.

FIG. 9 is a partly sectional end view of a finger 136 with two of the devices 80 holding bone pins 82 in engagement with bone fragments 138. Two or more of the devices 80 may be used in this way so that the bone pins 82 can be directed from various locations extending around the bone fragments.

While the pin holders 96, 134 have been described in terms of use with the device 90 of FIGS. 5-7, it is understood that such pin holders 96, 134 can alternately be used with a device otherwise as described above in reference to FIGS. 1-3, with deformable portions 98, 150 being deflected in response to tightening the clamping member 30 to hold pins in place within the pin holders 56, 134.

FIG. 10 is a cross-sectional side elevation of a device 160 built in accordance with a second version of the second embodiment of the invention to include a housing 162 having both a first internal mounting surface 164 holding a plurality of pin holders 52 in a first row 166 and a second internal mounting surface 168 holding a plurality of pin holders 52 in a second row 170. The device 160 additionally includes a first clamping device 172, which is turned to clamp and release all of the pin holders 52 in the first row 166, and a second clamping device 174, which is used to clamp and release all of the pin holders 52 in the second row 170. Other features of the device 100 are as described above in reference to FIGS. 5-9 for the device 80 built in accordance with the first version of the second embodiment of the invention. While the example of FIG. 10 shows three pin holders 52 held within each of the internal mounting surfaces 168, it is understood that each of the internal mounting surfaces in general can be configured to hold two or more pin holders 52.

While a small example of the device 80 has been shown in FIG. 5, being applied for the fixation of bones within a finger, it is understood that the device 80 and the device 160 of FIG. 2 may be built in any size, having any number of pin holders 96, for the fixation of bone fragments in any long bones, including the tibia and the humerus. While the invention has been described in terms of preferred embodiments and versions thereof with some degree of specific, it is understood that this description has been given only by way of example, and that many changes can be made without departing from the spirit and scope of the invention, as described in the appended claims.

What is claimed is:

1. Apparatus for external fixation of bone fragments, wherein the apparatus comprises:
    a housing including an internal mounting surface and an aperture;
    a pin holder held within the housing, including a spherically rounded external surface engaging the internal mounting surface within the housing, a pin mounting hole extending in a straight line through a center of the spherical rounded external surface between first and second ends of the pin holder, and a first slot, disposed along a plane perpendicular to the pin mounting hole to extend outward from the pin mounting hole in all directions perpendicular to the pin mounting hole, extending across the pin mounting hole and partially across the pin holder, displaced inward from a first end of the pin mounting hole, forming a first deflectable portion of the pin holder extending between the first slot and the first end of the pin mounting hole;
    a bone pin, held within the pin mounting hole of the pin holder to extend through the aperture, wherein an angle, relative to the housing, at which the bone pin extends through the aperture is varied by pivoting the pin holder within the housing, and
    a clamping member holding the pin holder in place within the housing and deflecting the first deflectable portion of the pin holder to hold the bone pin in place within the pin holder.

2. The apparatus of claim 1, wherein the pin holder additionally includes a second slot, disposed along a plane perpendicular to the pin mounting hole to extend outward from the pin mounting hole in all directions perpendicular to the pin mounting hole, extending across the pin mounting hole and partially across the pin holder, displaced inward from a second end of the pin mounting hole, opposite the first end of the pin mounting hole, forming a second deflectable portion of the pin holder extending between the second slot and the second end of the pin mounting hole.

3. The apparatus of claim 2, wherein
    the clamping member includes a threaded surface and an annular surface engaging the first deflectable portion of the pin holder,
    the housing includes a threaded surface disposed adjacent the aperture,
    the threaded surface of the clamping member engages the threaded surface of the housing,
    the pin holder includes a central part extending between the first and second slots,
    as the clamping member is rotated in a first direction, an engagement force between the spherically rounded surface of the pin holder and the internal mounting surface within the housing is increased to hold the pin holder in place within the housing, and deflection of the first and second deflectable portions of the pin holder is increased, moving a portion of the pin mounting hole within each of the first and second deflectable portions out of alignment with a portion of the pin mounting hole extending through the central part of the pin holder to hold the bone pin in place within the pin holder, and
    as the clamping member is rotated opposite the first direction, the engagement force between the spherically rounded surface of the pin holder and the internal mounting surface within the housing is decreased to allow rotation of the spherically rounded surface of the pin holder within the internal surface of the housing, and the deflection of the first and second deflectable portions is decreased, returning the portions of the pin mounting hole within the first and second deflectable portions into alignment with the portion of the pin mounting hole extending through the central part of the pin holder to allow movement of the bone pin within the pin holder.

4. The apparatus of claim 1, wherein the housing includes a plurality of internal mounting surfaces and a plurality of apertures, and wherein the apparatus comprises:
    a plurality of pin holders held within the housing, each including a spherically rounded external surface engaging one of the internal mounting surfaces within the housing, a pin mounting hole extending in a straight line through a center of the spherical rounded external surface, and a first slot, disposed along a plane perpendicular to the pin mounting hole to extend outward from the pin mounting hole in all directions perpendicular to the pin mounting hole, extending across the pin mounting hole and partially across the pin holder, displaced inward from a first end of the pin mounting hole, forming a first deflectable portion of the pin holder extending between the first slot and the first end of the pin mounting hole;
    a plurality of bone pins, each held within the pin mounting hole of a pin holder in the plurality of pin holders to extend through an aperture in the plurality of apertures, wherein an angle, relative to the housing, at which each bone pin in the plurality of bone pins extends through an aperture in the plurality of apertures is varied by pivoting the pin holder within the housing, and
    a plurality of clamping members, each holding a pin holder in the plurality of pin holders in place within the housing and deflecting the first deformable portion the pin holder to hold a bone pin in the plurality of bone pins in place within the pin holder.

5. The apparatus of claim 4, wherein the housing comprises:
a vertically elongated central portion including a first plurality of the internal mounting surfaces; and
a lateral portion extending outward and rearward from each side of an upper end of the vertically elongated central portion, wherein each lateral portion includes at least one of the internal mounting surfaces.

6. The apparatus of claim 4 wherein
each clamping member in the plurality of clamping members includes a threaded surface and an annular surface engaging the first deflectable portion of a pin holder in the plurality of pin holders,
the housing includes a plurality of threaded surfaces, each disposed adjacent an aperture in the plurality of apertures,
the threaded surface of each of the clamping members engages one of the threaded surfaces of the housing,
each pin holder in the plurality of pin holders includes a central part extending adjacent the first slot and away from the first deflectable portion,
as each of the clamping members is rotated in a first direction, an engagement force between the spherically rounded surface of the pin holder clamped in place within the housing by the clamping member and an internal mounting surface in the plurality of internal mounting surfaces within the housing is increased to hold the pin holder in place within the housing, and deflection of the first deflectable portion of the pin holder is increased, moving a portion of the pin mounting hole within the first deflectable portion out of alignment with a portion of the pin mounting hole extending through the central part of the pin holder to hold the bone pin in place within the pin holder, and
as each of the clamping members is rotated opposite the first direction, the engagement force between the spherically rounded surface of the pin holder clamped in place within the housing by the clamping member and an internal mounting surface in the plurality of internal mounting surfaces within the housing is decreased, to allow rotation of the spherically rounded surface of the pin holder within the internal mounting surface of the housing and deflection of the first deflectable portion is decreased, returning the portion of the pin mounting hole within the first deflectable portion into alignment with the portion of the pin mounting hole extending through the central part of the pin holder to allow movement of the bone pin within the pin mounting hole of the pin holder.

7. The apparatus of claim 6, wherein the housing comprises:
a vertically elongated central portion including a first plurality of the internal mounting surfaces; and
a lateral portion extending outward and rearward from each side of an upper end of the vertically elongated central portion, wherein each lateral portion includes at least one of the internal mounting surfaces.

8. The apparatus of claim 6, wherein each of the pin holders in the plurality of pin holders additionally comprises a second slot, perpendicular to the pin mounting hole, extending across the pin mounting hole and partially across the pin holder, displaced inward from a second end of the pin mounting hole, forming a second deflectable portion of the pin holder extending between the second slot and the second end of the pin mounting hole.

9. The apparatus of claim 8 wherein
as each of the clamping members is rotated in a first direction, deflection of the second deflectable portion of the pin holder is increased, moving a portion of the pin mounting hole within the second deflectable portion out of alignment with a portion of the pin mounting hole extending through the central part of the pin holder,
as each of the clamping members is rotated opposite the first direction, the portion of the pin mounting hole within the second deflectable portion is returned into alignment with the portion of the pin mounting hole extending through the central part of the pin holder to allow movement of the bone pin within the pin mounting hole of the pin holder.

10. Apparatus for external fixation of bone fragments, wherein the apparatus comprises:
a housing including an internal mounting surface, an aperture, and a threaded surface disposed adjacent the aperture;
a pin holder held within the housing, including a spherically rounded external surface engaging the internal mounting surface within the housing, a pin mounting hole extending in a straight line through a center of the spherical rounded external surface between first and second ends of the pin holder, and a first slot, perpendicular to the pin mounting hole, extending across the pin mounting hole and partially across the pin holder, displaced inward from a first end of the pin mounting hole, forming a first deflectable portion of the pin holder extending between the first slot and the first end of the pin mounting hole; and a central part extending adjacent the first slot and away from the first deflectable portion;
a bone pin, held within the pin mounting hole of the pin holder to extend through the aperture, wherein an angle, relative to the housing, at which the bone pin extends through the aperture is varied by pivoting the pin holder within the housing, and
a clamping member holding the pin holder in place within the housing and deflecting the first deflectable portion of the pin holder to hold the bone pin in place within the pin holder, wherein
the clamping member includes a threaded surface and an annular surface engaging the first deflectable portion of the pin holder,
the threaded surface of the clamping member engages the threaded surface of the housing,
as the clamping member is rotated in a first direction, an engagement force between the spherically rounded surface of the pin holder and the internal mounting surface within the housing is increased to hold the pin holder in place within the housing, and deflection of the first deflectable portion of the pin holder is increased, moving a portion of the pin mounting hole within the first deflectable portion out of alignment with a portion of the pin mounting hole extending through the central part of the pin holder to hold the bone pin in place within the pin holder, and
as the clamping member is rotated opposite the first direction, the engagement force between the spherically rounded surface of the pin holder and the internal mounting surface within the housing is decreased to allow rotation of the spherically rounded surface of the pin holder within the internal surface of the housing and wherein the deflection of the first deflectable portion of the pin holder is decreased, returning the portion of the pin mounting hole within the first deflectable portion into alignment with the portion of the pin mounting hole extending through the central part of the pin holder to allow movement of the bone pin within the pin holder.

* * * * *